United States Patent [19]
Boettcher et al.

[11] Patent Number: 5,464,986
[45] Date of Patent: Nov. 7, 1995

[54] FLUORESCENT SPECTRAL DIFFERENTIAL MEASUREMENT OF A SUBSTRATE COATING

[75] Inventors: Jeffrey A. Boettcher, Falcon Heights; Lanny L. Harklau, Stillwater, both of Minn.

[73] Assignee: Minnesota Mining and Manufacturing Company, St. Paul, Minn.

[21] Appl. No.: 193,428

[22] Filed: Feb. 8, 1994

[51] Int. Cl.⁶ .................................................. G01N 21/64
[52] U.S. Cl. .................. 250/459.1; 250/302; 250/458.1; 250/461.1
[58] Field of Search .................... 250/458.1, 459.1, 250/461.1, 302; 356/381

[56]  References Cited

U.S. PATENT DOCUMENTS

| 3,723,008 | 3/1973 | Fukuda et al. | |
|---|---|---|---|
| 3,737,234 | 6/1973 | Shibata et al. | |
| 3,832,555 | 8/1974 | Ohnishi | 250/458.1 |
| 3,843,259 | 10/1974 | Tohyama et al. | |
| 3,843,259 | 10/1974 | Tohyama et al. | |
| 3,956,630 | 5/1976 | Mellows | 250/302 |
| 4,153,369 | 5/1979 | Kallet et al. | 356/318 |
| 4,250,382 | 2/1981 | Libby | 250/302 |
| 4,841,156 | 6/1989 | May et al. | 250/461.1 |
| 4,877,965 | 10/1989 | Dandliker et al. | 250/458.1 |
| 4,922,113 | 5/1990 | Melancon | 250/458.1 |
| 4,978,731 | 12/1990 | Malancon et al. | 528/15 |
| 5,087,670 | 2/1992 | Melancon et al. | 525/326.2 |

FOREIGN PATENT DOCUMENTS

| 819647 | 4/1981 | U.S.S.R. |
| 1539608 | 1/1990 | U.S.S.R. |

*Primary Examiner*—Carolyn E. Fields
*Attorney, Agent, or Firm*—Patterson & Keough

[57] ABSTRACT

A fluorescent spectrophotometer measures the fluorescent characteristics of fluorescent probes within functional compositions of a specimen. The fluorescent spectrophotometer emits light appropriate for exciting the fluorescer or fluorescers contained within the specimen. The excited fluorescer emits within an emission wavelength spectrum. Fluorescers having a narrower wavelength region over which an abrupt change in emission intensity occurs are chosen for use as a fluorescent probe. The fluorescent spectrophotometer detects the change in intensity through this narrower area and performs a derivative calculation on the intensity curve. The fluorescent spectrophotometer is able to distinguish the fluorescer from other fluorescers or interfering fluorescent backgrounds.

33 Claims, 8 Drawing Sheets 5,464,986

FLUORESCENT SPECTRAL DIFFERENTIAL MEASUREMENT OF A SUBSTRATE COATING

CROSS REFERENCE TO CO-PENDING APPLICATIONS

This invention is related to, and filed concurrently with, U.S. patent application Ser. No 08/193,599, assigned to the same assignee.

1. Field of the Invention

The present invention relates generally to spectroscopic measurement of fluorescent compounds and particularly to exploiting a characteristic of a class of fluorescent compounds that are readily identified from a first derivative analysis of the emissions spectrum of the fluorescent compound.

2. Background of the Invention

In the discussion below, the term "fluorescence" refers to luminescence in general and encompasses fluorescence and phosphorescence.

Fluorescent spectrophotometry refers to those devices and methods used for measuring the intensity or the wavelength spectra of the fluorescent light emitted from a fluorescent compound. The purpose for measuring these emissions is to analyze the measured material qualitatively or quantitatively. A representative method is disclosed in U.S. Pat. No. 4,922,133 issued to Melancon where fluorescent probes are added to functional compositions or coatings and the intensity of fluorescence is correlated to the weight or thickness of the functional composition.

In general, a fluorescent spectrophotometer includes a light source having an output wavelength suitable for exciting a fluorescent compound. The output light from the light source is directed onto the material specimen raising the electron state of the fluorescent compound contained within the material specimen. Fluorescence occurs when the shifted electron returns to its previous state emitting photons of radiant energy. Light emitted from the fluorescent compound is collected and directed toward a spectrophotometer or monochromator for dispersing the emitted fluorescent light into monochromatic wavelengths. The monochromated light is directed at a photodetector and the intensity and wavelength of the light can be tested and measured. Fluorescent spectrophotometry is well known in the art and represented in U.S. Pat. No. 3,832,555 issued to Ohnishi. U.S. Pat. No. 4,877,965 issued to Dandliker et al. discloses a time gated method of acquisition of fluorescent light as a method for discriminating the fluorescence from unwanted background noise.

The existing art is not capable of distinguishing two or more fluorescent emissions sources with similar overlapping emissions spectra. Where there is a need to measure more than one component, existing practice is to employ dissimilar fluorescent compounds. This necessitates the use of multiple light sources, monochromators, detectors, and associated optics.

SUMMARY OF THE INVENTION

The invention comprises a method for measuring a fluorescent emission value of a functional coating of a substrate. The method comprises the steps of providing a functional coating with an effective amount of a fluorescer that absorbs radiant energy in a wavelength range A and emits radiant energy in an emission wavelength range B and contains within the emission wavelength range B a narrower wavelength range C wherein the amount of emitted radiant energy changes abruptly from the emission in that part of range B which is just below range C and the emission in range C. The functional coating is excited with radiant energy of the wavelength of range A and the radiant energy emissions of wavelength range B, including the wavelength range C emitted by the functional coating are detected. A derivative calculation of the detected wavelength range C is performed to obtain a differential change in radiant energy emissions of the functional coating.

The invention also comprises an apparatus to detect the fluorescent emissions of a functional composition applied to all or part of a substrate having a known absorption wavelength range and a known emission wavelength range. The system comprises fluorescer means with an emissions wavelength range containing an included narrower fluorescent emissions wavelength range within which the intensity of the emissions changes abruptly. This narrower range is useful for measuring the fluorescent emissions intensity of a functional coating containing the fluorescer. Detection means is adjusted to the narrower included fluorescent wavelength range of the fluorescer detects the level of fluorescent emissions in this narrower included wavelength range when radiant energy in the absorption wavelength range of the fluorescer excites the fluorescer. An analyzer analyzes the fluorescent emission change of the narrower included fluorescent wavelength range to obtain a value and a correlator correlates the value obtained from analysis of the fluorescent emissions intensity to a physical characteristic of the functional coating.

BRIEF DESCRIPTION OF THE DRAWINGS

FIG. 1b is a graphic representation of the first derivative of the curve in FIG. 1a.

FIG. 3b is a graphic representation of the first derivatives of each curve in FIG. 3a.

DETAILED DESCRIPTION OF THE INVENTION

Figure 1A:
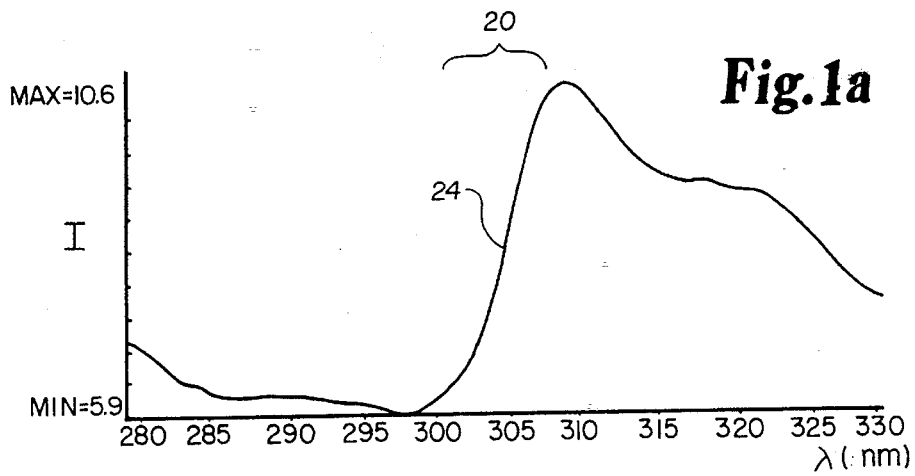
FIG. 1a is a graphic representation of the emissions wavelength spectrum for 9-ICF.

The graph of FIG. 1a depicts the fluorescent intensity curve for the emissions spectrum of 9-isocyantofluorene (9-ICF) through the wavelength range from 280 nm out to 330 nm. Using existing methods and systems, if 9-ICF is the only fluorescent compound emitting in the wavelength region being detected, then a single simple measurement of emission output intensity at any point within the emissions wavelength range is representative of the amount of 9-ICF within the functional composition, for example a thin film. However, the present invention is a different apparatus and method for evaluating the emissions output of a fluorescer and is especially useful in those circumstances where there is more than one fluorescent compound emitting in the same or similar overlapping emissions output wavelength range.

Figure 1B:
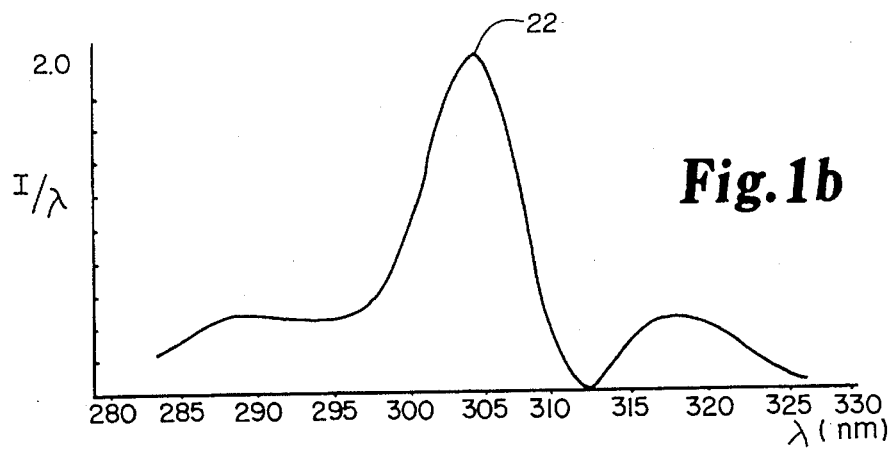

In FIG. 1a, a region 20 depicts approximately a 7 nm spectrum range from 302 nm to 309 nm. Within region 20 there is an abrupt change in emissions intensity from 9-ICF. As depicted in FIG. 1b, performing a first order derivative, or differential, on the curve in FIG. 1a produces a dramatic peak 22 centered on about peak slope point 24 corresponding to the 305 nm wavelength. The curve immediately to either side of peak 22 and bounded by region 20 represents the change in the slope of the emissions output curve depicted in FIG. 1a through region 20. The curve in FIG. 1b is representative of the emissions output for 9-ICF. Since it was 9-ICF that caused the change in emissions output through range 20, the values obtained for the peak slope of the curve in FIG. 1b can be compared to known standards of various concentrations of 9-ICF to obtain the absolute amount of 9-ICF detected. If 9-ICF is used as a fluorescent probe in a functional composition then the thickness or weight of the functional composition is determinable by knowing the concentration of 9-ICF in the functional composition after applied to a substrate.

Some circumstances encounter more than one fluorescent compound. If the emissions spectra for the fluorescent compounds overlap then each fluorescent compound will compete or interfere against the others. Existing art using the simple single measurements of an emissions output at any of the wavelengths within the overlapping emissions wavelength range will not be able to distinguish the individual contributions made by each of the competing compounds.

Figure 2:
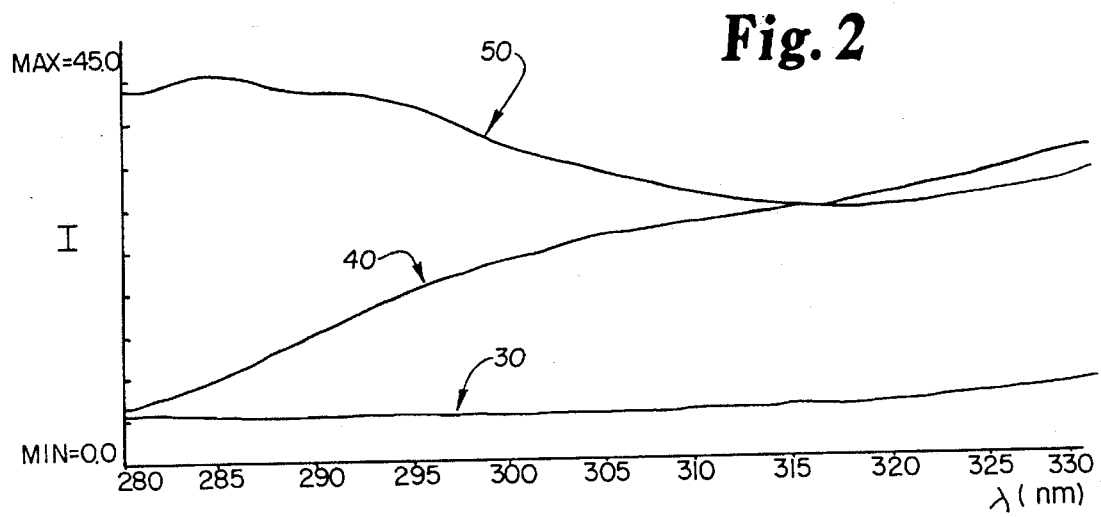
FIG. 2 is a graphic representation of the emissions wavelength spectra of several hot melt adhesives.

A practical limitation due to competing or interfering fluorescent compounds is evident in FIG. 2 depicting the emissions output curves 30, 40 and 50 for three different hot melt adhesives. These hot melts are used as adhesive backing to a substrate which can either be a thin film itself or a substrate for an additional application of thin films. As is evident from the fluorescent emission curves in FIG. 2, hot melts vigorously fluoresce throughout the 285 nm to 330 nm range. A fluorescent probe, such as 9-ICF, mixed within a functional composition, is a weak fluorescent emitter by comparison to the strongly emitting hot melt adhesives represented by curves 30, 40 and 50.

Figure 3A:
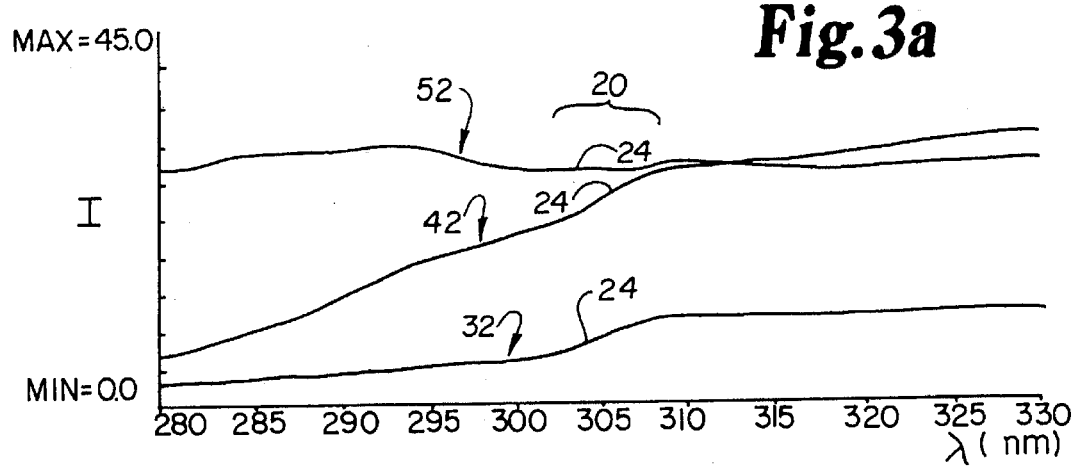
FIG. 3a is the emissions wavelength spectra of the same several hot melt adhesives with the addition of the fluorescer 9-ICF as a fluorescent probe.

FIG. 3a depicts the respective emissions output intensity curves 32, 42 and 52 containing the addition of the 9-ICF fluorescent probe as a thin film functional coating with each hot melt adhesive. The additional effects of the 9-ICF fluorescent probe are virtually undetectable against the competing background emissions, even through the narrower wavelength range of region 20. Consequently, a fluorescent probe and any other component of the product that emits within the same broad wavelength band of emissions will compete throughout that broad wavelength band. The fluorescent probe will likely be undetectable by existing means.

Figure 3B:
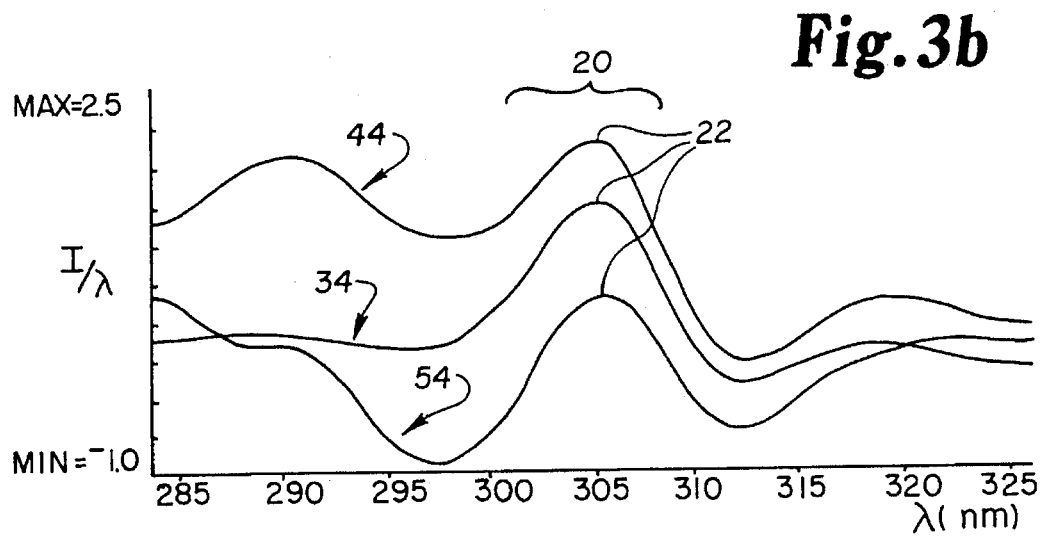

FIG. 3b depicts the present invention's ability to detect the abrupt change in fluorescent emissions output contributed by fluorescent probe 9-ICF despite the competing emissions of the hot melt adhesives. As depicted in FIG. 3b, first order derivative curves 34, 44 and 54, or differentials, are plotted from the respective emissions curves 32, 42 and 52 of FIG. 3a. The peaks occurring at point 22, the 305 nm wavelength, for each hot melt plus fluorescer probe corresponds to the peak for 9-ICF as demonstrated in FIG. 1b. Point 22 of curves 34, 44 and 54 in FIG. 3b represent the peak slope point 24 of the emission curves 32, 42 and 52 of FIG. 3a. The fluorescent intensity of the 9-ICF probe is proportional to the peak slope minus the average of the side slopes. Consequently, the peak slope is also directly proportional to the amount of 9-ICF present in the functional coating. Since the concentration of the fluorescent probe 9-ICF in the functional coating will be known, the intensity of 9-ICF will be proportional to the total amount of functional coating applied as a thin film to the substrate.

It is recognized that, within the context of this invention, functional coatings or compounds may be selected for/from various uses. Some uses include protective coatings, adhesive backside coatings, radiation-sensitive imageable coatings, priming coatings, release coatings, and barrier coatings. Preferred coatings permit flourescent probes for use in the coatings to be chemically bound to the coatings, soluble in the coating, or dispersed in the coating composition. Proper selection of coatings and probes, when utilized according to the teachings of this invention, permit correlation of the derivative values of emissions to certain characteristic(s) of the coating(s). These characteristics include, for example, thickness, weight, uniformity, defects, and other markings.

Many manufacturing processes can use multiple fluorescent probes within the different functional compounds as aids to measuring the weight or thickness of each functional compound. In this way, one can have manufacturing control and quality assessment as each functional compound is added to the product. The ability to detect similar competing fluorescers used as probes allows the convenience of working within the same wavelength region. As an example, each fluorescer 9-ICF, α-NPO, and Uvitex OB are excited at 325 nm. Thus, only a single light source for excitation of the probes is needed and only a single monochromator and detector are likewise needed.

If unable to use similar and thus competing fluorescers, then the fluorescent probes must operate in dissimilar wavelength ranges each requiring its own setup for excitation and emissions detection in separate portions of the spectrum. Use of dissimilar probes often requires using one probe that absorbs and emits in the ultraviolet range and a second probe that both absorbs and emits below the absorption and emissions of the first probe. This avoids inappropriate excitation of the second probe and undue quenching of the first probe as a consequence of the second probe absorbing the emissions of the first probe. The second probe is usually from a group that absorbs and emits in the visible spectrum. Unfortunately, use of fluorescent probes that emit in the visible spectrum will also affect the color purity and clarity of the final product which may be undesirable. Circumstances of manufacture may require the application of more than one functional composition. Existing methods do not provide for, or anticipate, simultaneous measurement of two fluorescent probes with overlapping emissions spectra.

Figure 4A:
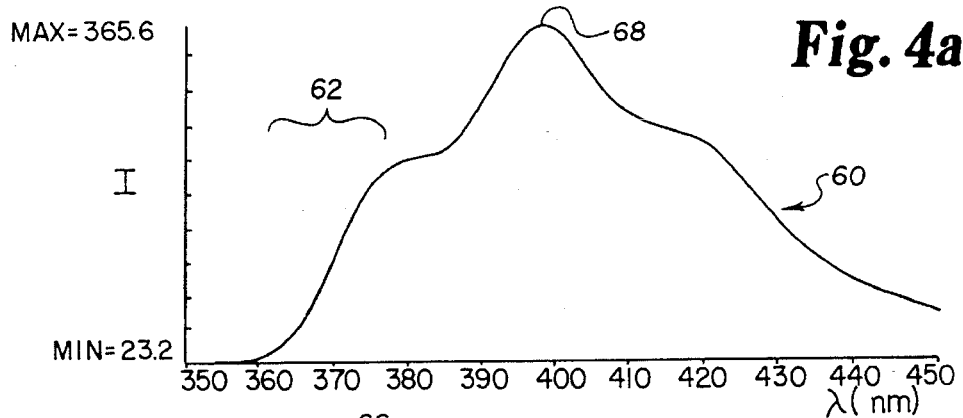
FIG. 4a is a graphic representation of the emissions wavelength spectrum for the fluorescer α-NPO.
Figure 4B:
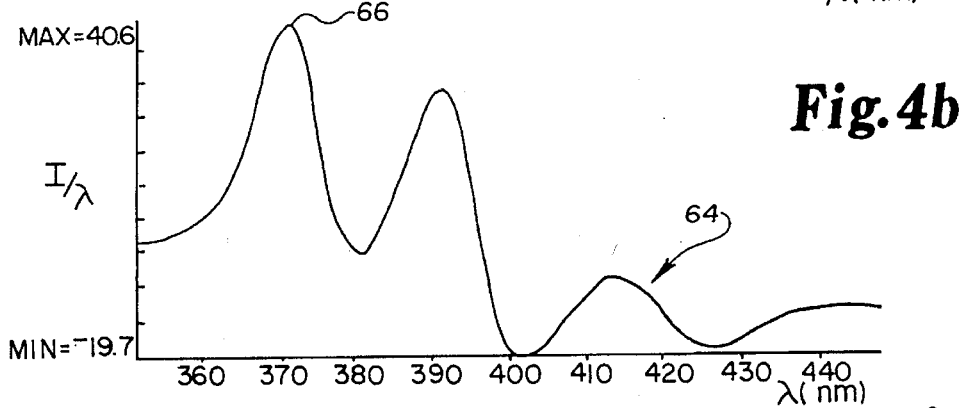
FIG. 4b is a graphic representation of the derivative of FIG. 4b.

Another embodiment of the present invention allows simultaneous discrimination and measurement of multiple fluorescent probes. FIG. 4a depicts an emissions curve 60, the emissions spectrum for the fluorescer α-NPO. A region 62 of curve 60 denotes a narrower wavelength range of curve 60 where fluorescent emissions change abruptly for α-NPO. FIG. 4b depicts curve 64 which is a first order derivative of curve 60 from FIG. 4a. A peak 66 of curve 64 corresponds to the abrupt change in emissions output and is representative of α-NPO.

Figure 4C:
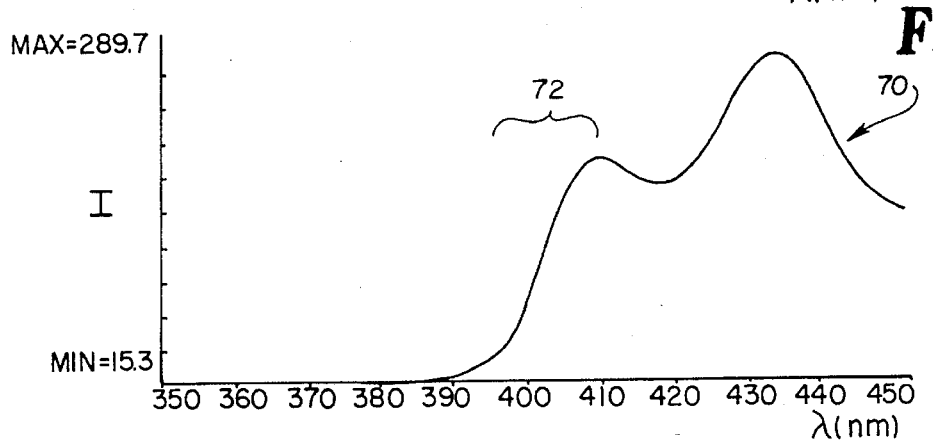
FIG. 4c is a graphic representation of the emissions wavelength spectrum for the fluorescer Uvitex OB.
Figure 4D:
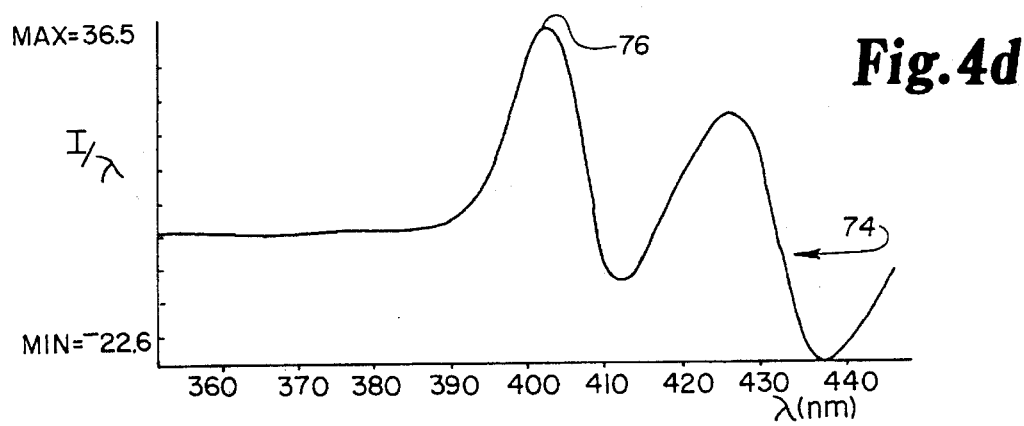
FIG. 4d is a graphic representation of the first derivative curve of the graph in FIG. 4c.

FIG. 4c depicts an emissions curve 70, the emissions spectrum for the fluorescer Uvitex OB. A region 72 of curve 70 denotes the narrower wavelength range of curve 70 where fluorescent emissions change abruptly for Uvitex OB. Note that region 72 of curve 70 includes the wavelength band of approximately 395 to 405 nm. From curve 60 in FIG. 4a, a point 68 corresponds to the peak emissions wavelength for α-NPO which is also in the wavelength range of curve 70 corresponding to region 72 in FIG. 4c. Existing methods would not be able to measure the presence of the fluorescer Uvitex OB in the presence of the fluorescer α-NPO. Due to this competition between these two fluorescent probes, existing methods would teach away from using these two fluorescers simultaneously.

Figure 4E:
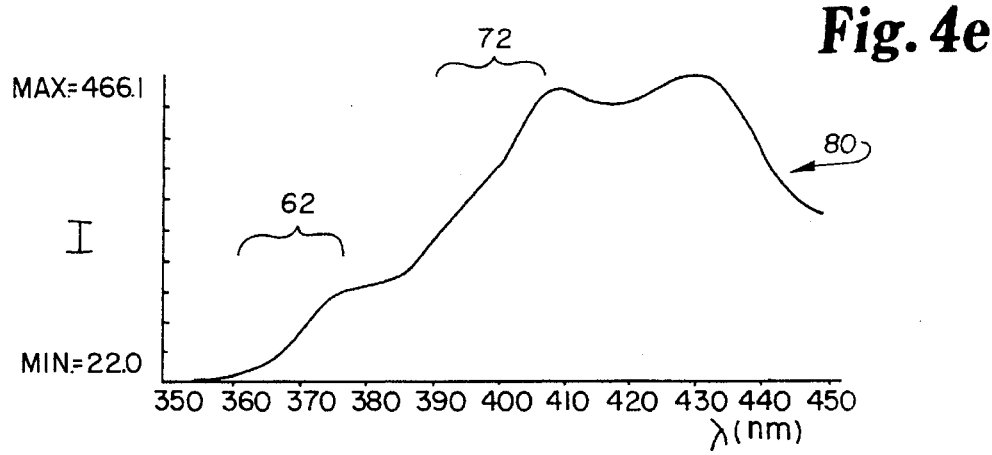
FIG. 4e is a graphic representation of the emissions wavelength spectrum for Kraton adhesive from two layers, one layer containing the fluorescer α-NPO, the second layer containing the fluorescer Uvitex OB as fluorescent probes.

FIG. 4e depicts an emissions curve 80 obtained from the fluorescers α-NPO and Uvitex OB used as fluorescent probes in separate functional coating layers of Kraton adhesive applied to a polypropylene thin film substrate. α-NPO is depicted at a concentration of 0.1% of solids and Uvitex OB is depicted at a concentration of 0.3% of solids. Kraton adhesive and polypropylene do not appreciably absorb or fluoresce in the wavelengths measured for these two fluorescent probes. In FIG. 4e, region 62 represents the abrupt change in fluorescent wavelength emissions for α-NPO, which is discernable but not useful. Region 72 corresponds to the abrupt change in fluorescent wavelength emissions for Uvitex OB and is indistinguishable from the peak emissions generated by α-NPO in this same wavelength range.

Figure 4F:
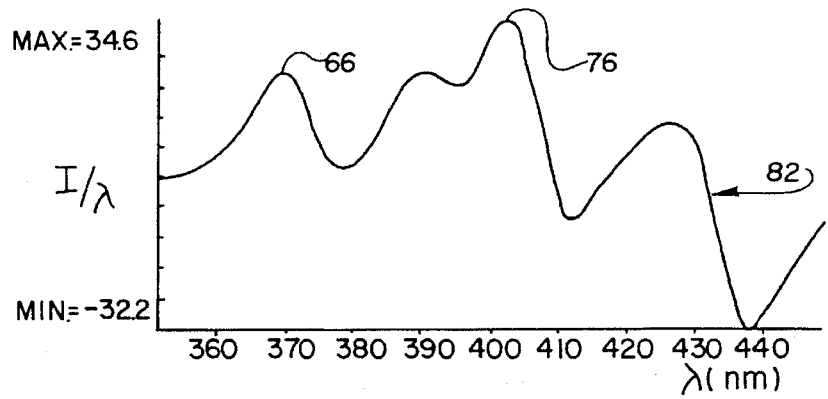
FIG. 4f is a graphic representation of the first derivative of the curve in FIG. 4e.

FIG. 4f depicts a curve 82 which is the first derivative of curve 80 from FIG. 4e. In FIG. 4f, peaks 66 and 76 representing α-NPO and Uvitex OB respectively are evident and easily measured. Since each peak is proportional to the amount of its respective fluorescer then each peak is proportional to the weight or thickness of the Kraton adhesive layer represented by each individual fluorescent probe applied to the polypropylene substrate.

Data suggests that for 9-ICF, α-NPO and Uvitex OB the invention is sufficiently sensitive to be able to detect a fluorescer with as little as a 1% change in the total emissions output over the narrower included wavelength range. The sharper or more dramatic the abrupt change in fluorescent output through this narrower range the more sensitive the detection. For a fluorescer with an abrupt change over approximately a narrow 15 nm wavelength range, the fluorescer should be of sufficient quantity or concentration in the functional composition to contribute to approximately a 5% change in the overall emissions intensity. For more abrupt changes approaching a narrower wavelength range of 3 nm, a change of only 1% from the overall emissions intensity is detectable. It is anticipated that other fluorescers are available or will be developed to take advantage of, and fall within the scope of, the present invention and also expand the sensitivity.

Figure 5:
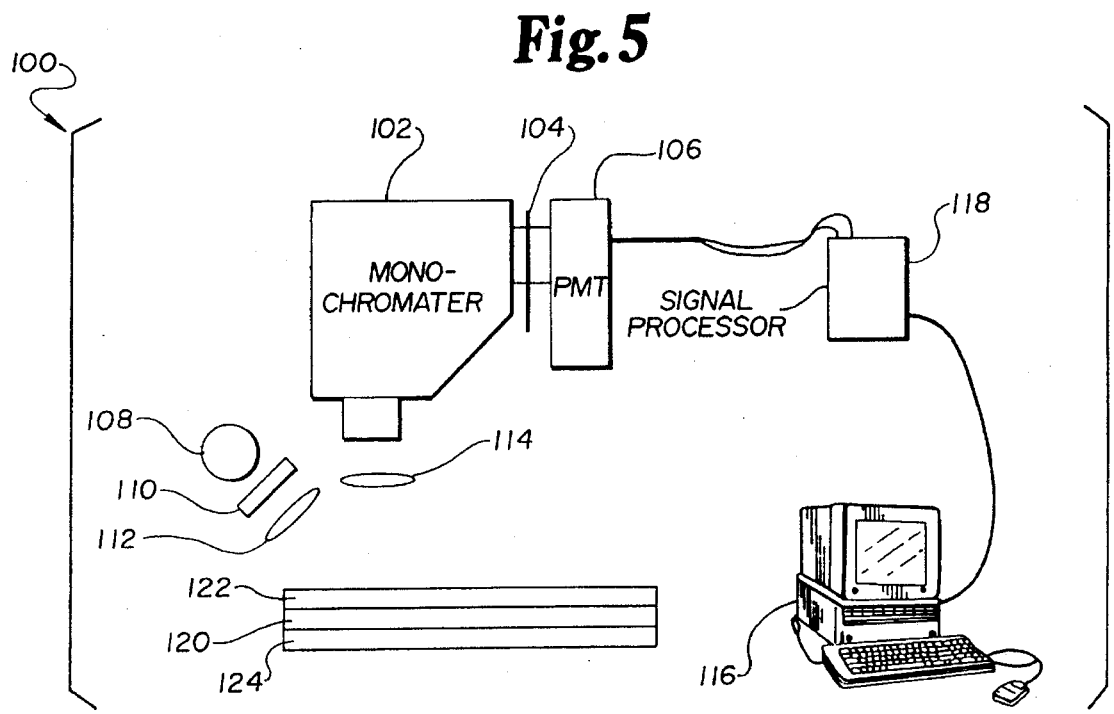
FIG. 5 is a schematic representation of an embodiment of the present invention.

FIG. 5 depicts an embodiment of the present invention as system 100 comprising a monochromator 102, a chopper 104, a photomultiplier tube (PMT) 106, a light source 108, an optical filter 110, a projection lens 112, an object lens 114, a computer subsystem 116, and a signal processor 118.

Light source 108 emits in a wavelength band suitable for exciting fluorescent probes in functional coatings and functional compositions such as a light adhesion coating 122, a backing substrate 120, and an adhesive 124. Alternatively, one or more layers 120, 122, or 124 may contain a compound that fluoresces in the same wavelength band and therefore competes with a fluorescer added as a measuring probe to another layer.

Optical filter 110 removes unwanted frequencies from the excitation light emitted from light source 108. Projection lens 112 focuses the excitation light to a spot on the material to be measured. The fluorescent emissions from the material are focused by object lens 114 into monochromator 102.

With the use of diffraction gratings and prisms, monochromator 102 separates the fluorescent emissions from the material being tested into discrete wavelengths which leave monochromator 102 through an exit slit and are directed to chopper 104. Chopper 104 in system 100 is a revolving wheel with a port aligned to scan past the exit slit of monochromator 102. As chopper 104 spins, the port will move past the exit slit of monochromator 102 allowing selected wavelengths to reach PMT 106. PMT 106 measures the intensity of light for each wavelength and a signal is sent to signal processor 118 which is linked directly with computer subsystem 116. Computer subsystem 116 performs all calculations and provides results for analysis.

Figure 6:
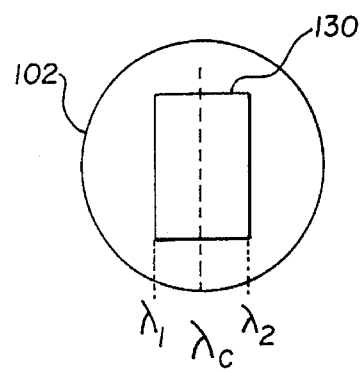
FIG. 6 is a side schematic view of an exit slit for a monochromator.

FIG. 6 depicts monochromator 102, as seen from the direction and perspective of chopper 106, having an exit slit 130. For system 100, a useful exit slit 130 has a resolution of 8 nm per mm of slit width. If a 4 mm wide exit slit 130 is used, then a 32 nm wavelength band width is dispersed at exit slit 130 at representative center wavelength $\lambda_c$ of monochromator 102. Representative border wavelengths $\lambda_1$ and $\lambda_2$ are 16 nm above and below $\lambda_c$ respectively.

There are several embodiments of the invention useful in distinguishing one or several fluorescent probes. Various embodiments are also useful for distinguishing fluorescent probes from an interfering background.

Figure 7:
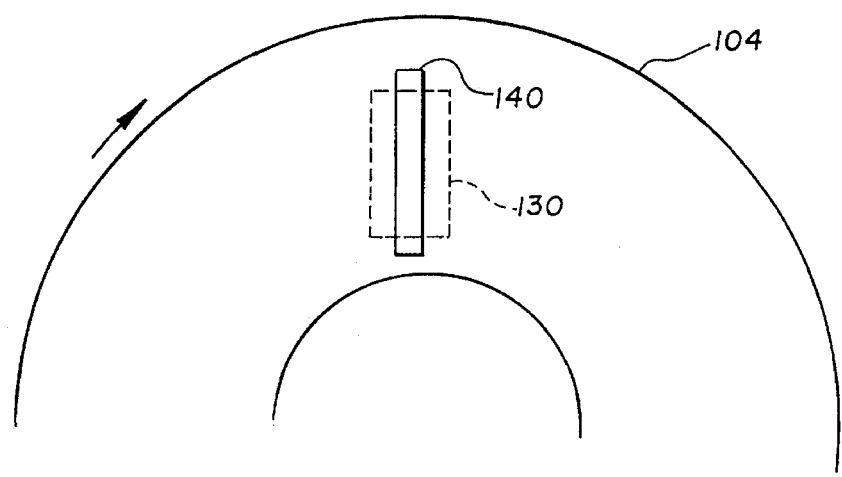
FIG. 7 is a schematic view on a narrow port chopper used

Referring to FIG. 7, an embodiment of the present invention uses a narrow port 140 in chopper 104 moving across exit slit 130 of monochromator 102. The representative wavelength $\lambda_c$ of exit slit 130 is chosen to correspond to the middle wavelength in the abrupt change region of the fluorescent probe to be detected. In this way the rapid transition spectrum region of the fluorescent probe is sampled. Using the 9-ICF emissions wavelength range as an example, monochromator 102 representative wavelength $\lambda_c$ would be centered at 305 nm and scan 16 nm above and below representative wavelength $\lambda_c$.

Figure 8A:
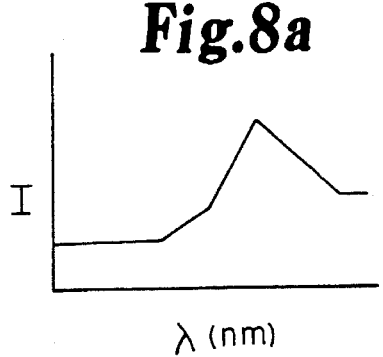
FIG. 8a is a graphic representation of a demonstrative emissions wavelength spectrum of a fluorescer.
Figure 8B:
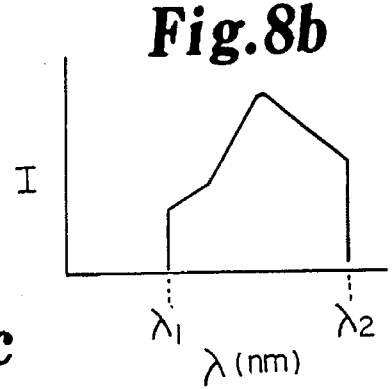
FIG. 8b is a graphic representation of the emissions wavelength spectrum obtained through a narrow port chopper.
Figure 8C:
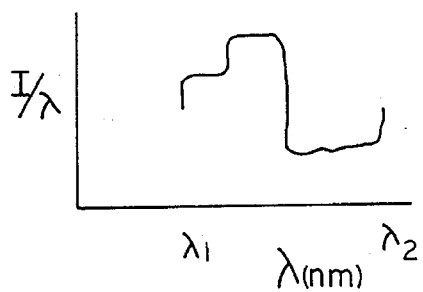
FIG. 8c is a graphic representation of the first derivative of the curve in FIG. 8b.

As narrow port 140 sweeps across exit slit 130 as shown in FIG. 7, the light intensity at each wavelength can be measured by PMT 106. This is graphically represented in FIGS. 8a and 8b. FIG. 8a graphs the emission spectrum of a hypothetical fluorescer. FIG. 8b is a graphic representation of the emissions output generated by revolving narrow port chopper 140. In FIG. 8b, $\lambda 1$ and $\lambda 2$ represent the upper and lower wavelength values chosen such that the narrow region of abrupt wavelength change is contained within the $\lambda 1$ and $\lambda 2$ boundaries. In the case of fluorescer 9-ICF and using a 32 nm band width at the exit port, $\lambda 1$ is 289 nm and $\lambda 2$ is 321 nm. FIG. 8c is the graphic representation of the first order derivative, or differential, taken of the values in FIG. 8b. The peak slope would be proportional to the amount of fluorescer within the functional composition.

Figure 9A:
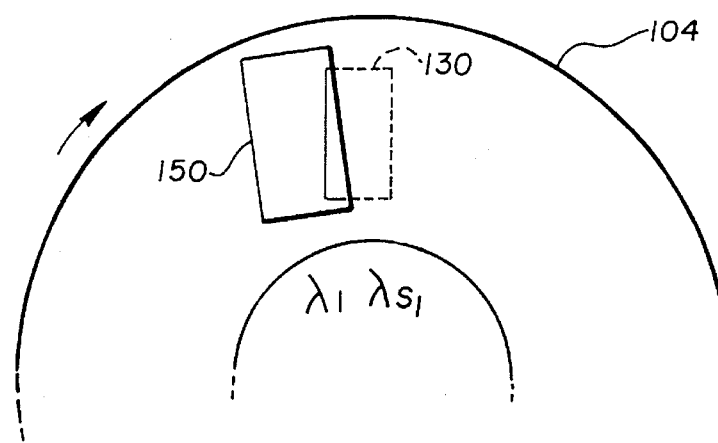
FIG. 9a is a schematic view of a wide port chopper as used in the invention.
Figure 9B:
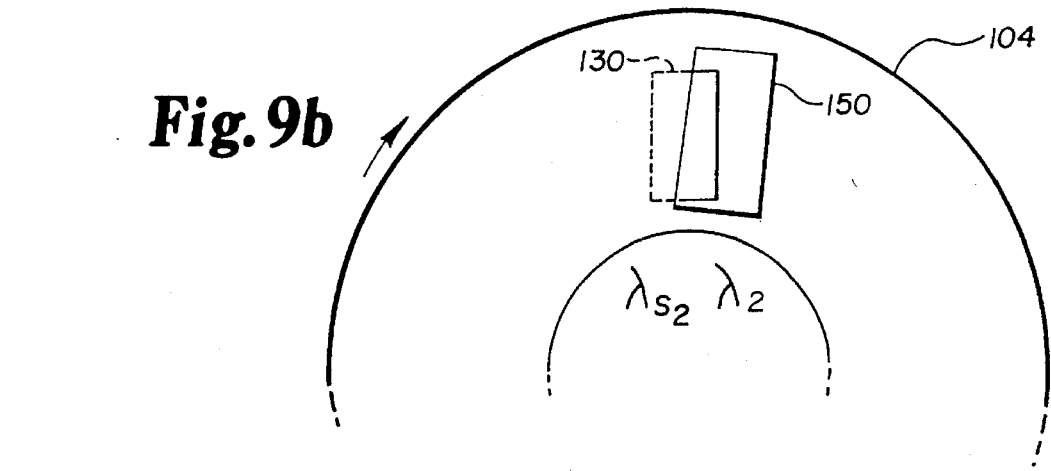
FIG. 9b is a view similar to FIG. 9a demonstrating the use of a wide port chopper.

Another technique is to use a wide port 150 as depicted in FIG. 9a that is slightly wider than exit slit 130 of monochromator 102. In this fashion the light intensity output is proportional to the integral fluorescent intensity value for that part of the spectrum output at exit slit 130. As shown in FIG. 9a, as wide port 150 approaches full exposure of all of exit slit 130, the light intensity measured by PMT 106 is proportional to the integral value of the fluorescent intensity measured from representative border wavelength $\lambda 1$ to the representative wavelength $\lambda_{s1}$ at thee leading edge of wide port 150. As wide port 150 begins decreasing the exposure of exit slit 130, as seen in FIG. 9b, the light intensity measured by PMT 106 is proportional to the integral value of the fluorescent intensity measured from representative wavelength $\lambda_{s2}$ at the trailing edge of wide port 150 to representative border wavelength $\lambda 2$.

Figure 10A:
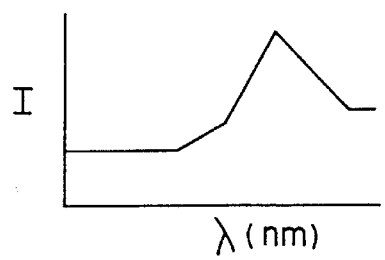
FIG. 10a is a graph of the emissions wavelength spectrum of a demonstrative fluorescer.
Figure 10B:
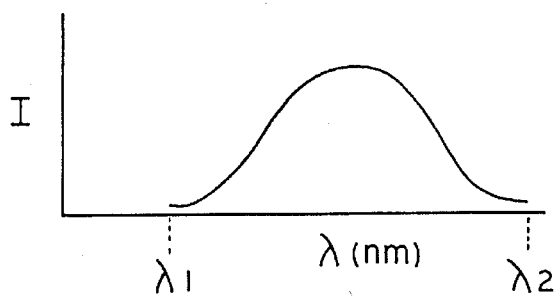
FIG. 10b is a graphic representation of the emissions wavelength spectrum output through a wide port chopper.
Figure 10C:
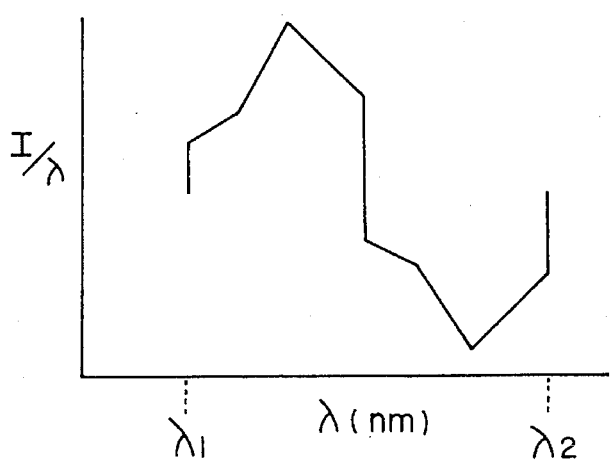
FIG. 10c is a graphic representation of the first derivative of the curve in FIG. 10b.
Figure 10D:
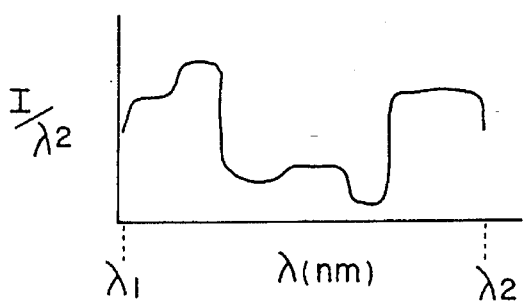
FIG. 10d is a graphic representation of the second derivative of the curve in FIG. 10c.

FIG. 10a graphs the fluorescent spectrum output intensity of a hypothetical fluorescer. However, wide port 150 produces the representative graph of the scan seen in FIG. 10b. Differentiating the signal graphed in FIG. 10b returns the original signal and its complement and produces the graph of FIG. 10c. Compare FIG. 10c to FIG. 8b. Differentiating the signal again will produce the plot represented by the graph of FIG. 10d. The peak slope value of FIG. 10d will be proportional to the concentration of the fluorescer within the functional composition. Compare FIG. 10d with FIG. 8c.

This wide port chopper technique is superior in performance to the narrow port chopper technique because of the significantly greater light intensities seen by PMT 106. This improves the signal-to-noise ratio. Since the overall effect contributed by the fluorescent probe to the total emissions of all components within the product may only change the total emissions by as little as 1%, the improved signal-to-noise characteristic of a wide port chopper technique improves the system's ability to accurately detect changes due solely to the emissions of the fluorescent probe. The wide port chopper technique requires the additional differential step, increasing the need for computing capacity.

Figure 11:
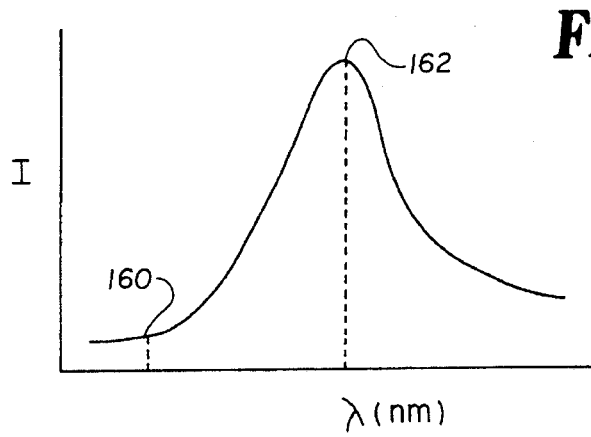
FIG. 11 is a graphic representation of the emissions wavelength spectrum for a demonstrative fluorescer.

Another technique uses a two point linear approximation. FIG. 11 depicts an emissions intensity curve. Two points 160 and 162 on the curve are chosen so that the slope of the line between the two points will closely approximate the peak slope value. In FIG. 11, the emissions intensity points 160 and 162 are determined and intensity is then calculated by the relationship:

intensity≈slope≈ (*I* at point 162 minus *I* at point 160)/(the wavelength of point 162 minus the wavelength of point 160).

Figure 12:
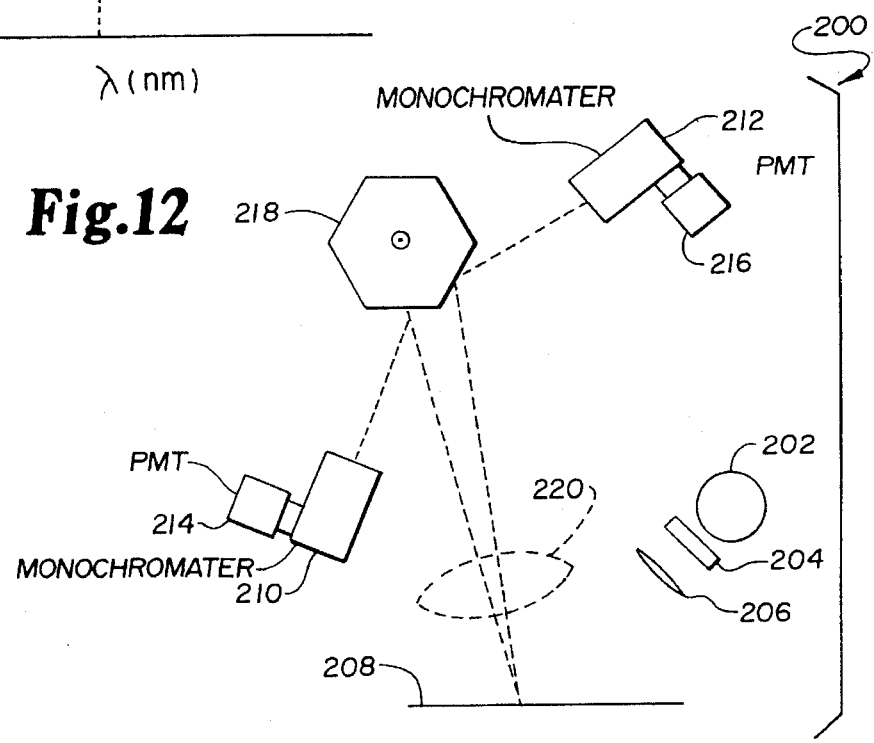
FIG. 12 is a schematic view of a system embodiment of the invention.

As depicted in FIG. 12, this technique is incorporated into apparatus 200, which includes a light source 202 with appropriate filter 204 and lens 206 to fluoresce product 208, two monochromators 210 and 212 adjusted to chosen wavelengths 160 and 162 respectively, photomultiplier tubes 214 and 216 to measure the intensities, and a rotating polygon mirror 218 with appropriate optics 220 to image the same point from product 208 surface into each monochromator 210 and 212. Outputs of photomultiplier tubes 214 and 216 are coupled to a computer, not shown, and are used to calculate the slope. An advantage shared by the narrow and wide port choppers over the two point linear approximation is the elimination of the second monochromator and the rotating mirror and optics to focus both monochromators on the same spot.

Figure 13:
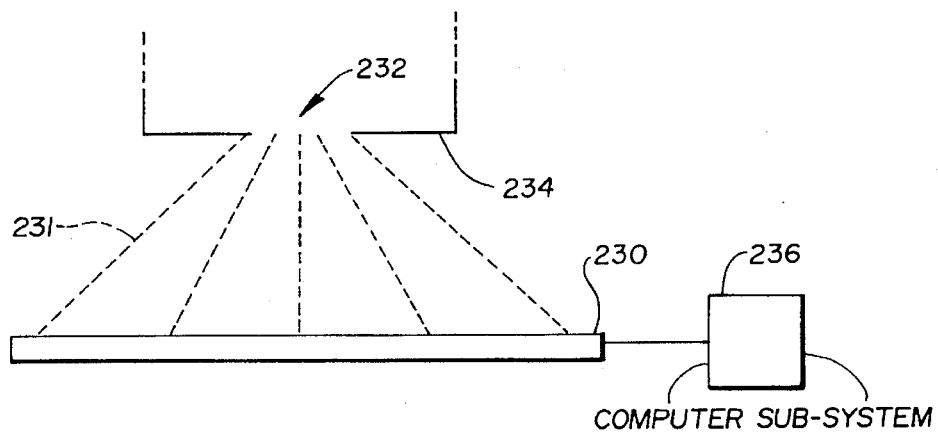
FIG. 13 is a side schematic view of an embodiment of the invention.

A fourth technique uses an optically sensitive linear array 230 as depicted in FIG. 13 that replaces the chopper wheel and photomultiplier tube. This system also works by allowing the light dispersion 231 from an exit slit 232 of a monochromator 234 to fall directly onto linear array 230. The outputs of the discrete elements of the array are fed to a computer subsystem 236 and generate a graph similar to the output for the narrow port chopper technique as depicted in FIGS. 8a, 8b, and 8c. The linear array technique would require only one differential computation step and eliminates most of the optical components. It is mechanically simpler as well. Drawbacks are differences in individual array elements and stability of the array as a whole.

We claim:

1. A method for measuring a fluorescent emission value of a functional coating of a substrate, comprising the steps of:
    providing a functional coating with an effective amount of a fluorescer that absorbs radiant energy in a wavelength range A, emits radiant energy in an emission wavelength range B, and contains within the emission wavelength range B a narrower wavelength range C; the amount of emitted radiant energy changing abruptly from the emission in that part of range B which is just below range C and the emission in range C;
    exciting the fluorescer with radiant energy of the wavelength of range A;
    detecting the radiant energy emissions of wavelength range B and the included wavelength range C emitted by the functional coating; and
    performing a derivative calculation of the detected wavelength range C to obtain a differential change in radiant energy emissions :of the functional coating.

2. The method of claim 1 in which the substrate fluoresces in approximately the same wavelength range as the emission wavelength of range B.

3. The method of claim 1 in which the wavelength range C is less than about 15 nanometers.

4. The method of claim 3 in which the wavelength range C is less than about 6 nanometers and the amount of change of radiant energy emission in wavelength range C changes by approximately 2% of the total emissions of the wavelength range B as measured immediately below the wavelength range C.

5. The method of claim 3 in which the wavelength range C is less than about 3 nanometers and the amount of change of radiant energy emission in wavelength range C changes by approximately 1% of the total emissions of the wavelength range B as measured immediately below the wavelength range C.

6. The method of claim 3 in which the wavelength range C is less than about 15 nanometers and the amount of change of radiant energy emission in wavelength range C changes by approximately 5% of the total emissions of the wavelength range B as measured immediately below the wavelength range C.

7. The method of claim 1 in which the fluorescer is an aromatic compound.

8. The method of claim 7 in which the aromatic compound is a fluorene compound.

9. The method of claim 1 in which the performing step comprises performing a first derivative calculation of the radiant energy emissions intensity of the wavelength range C.

10. The method of claim 9 in which the performing step further comprises performing a second derivative calculation of the radiant energy emissions intensity of the wavelength range C.

11. The method of claim 1 further comprising the step of sampling at two discrete wavelengths within the narrower wavelength range C to represent a minimum and a maximum level of emission intensity within the wavelength range C which results in a two point linear approximation.

12. The method of claim 1 further comprising the step of scanning the spectrum of the wavelength range C.

13. The method of claim 12 in which the step of scanning the spectrum of the wavelength range C comprises using a narrow port chopper.

14. The method of claim 12 in which the step of scanning the spectrum of the wavelength range C comprises using a wide port chopper.

15. The method of claim 12 in which the step of scanning the spectrum of the wavelength range C comprises using a photo-sensitive linear array.

16. The method of claim 1 further comprising the step of selecting the functional coating from protective coatings, adhesive coatings, priming coatings, low adhesion backside coatings, radiation-sensitive imageable coatings, release coatings, and barrier coatings.

17. The method of claim 1 in which the fluorescer is chemically bound to said functional coating composition.

18. The method of claim 1 in which the fluorescer is soluble in the functional coating composition.

19. The method of claim 1 in which the fluorescer is dispersed in the functional coating composition.

20. The method of claim 1 further comprising the step of correlating the derivative calculation to at least one characteristic of the functional coating.

21. The method of claim 20 further comprising the step of selecting the characteristic of the functional coating ! from a group of characteristics including thickness, weight, uniformity, defects, and markings.

22. The method of claim 1 in which the mean wavelength of range A is below the mean wavelength of range B.

23. A spectrophotometric apparatus to detect the fluorescent emissions of a functional composition applied to all or part of a substrate having a known absorption wavelength range and a known emission wavelength range, the apparatus comprising;

fluorescer means for measuring a fluorescent emissions intensity of a functional coating containing the fluorescer, said fluorescer means having an emissions wavelength range containing a narrower included fluorescent emissions wavelength range within which the intensity of fluorescent emission changes abruptly;

adjustable detection means adjusted to the narrower included fluorescent wavelength range of the fluorescer for detecting the level of fluorescent emissions in this narrower included wavelength range when radiant energy in the absorption wavelength range of the fluorescer excites the fluorescer;

analysis means for analyzing the fluorescent emission change of the narrower included fluorescent wavelength range to obtain a value the analysis means including means for taking a first derivative calculation of the fluorescent emissions of the narrower included wavelength range; and correlation means for correlating the value obtained from analysis of the fluorescent emissions intensity to a physical characteristic of the functional coating.

24. The apparatus of claim 23 in which the narrower included emission wavelength range is less than about 15 nanometers.

25. The apparatus of claim 23 in which the narrower included wavelength range is less than about 6 nanometers and changes the total emissions by approximately 2% as measured from the total fluorescent emissions at a wavelength just below the narrower included wavelength range.

26. The apparatus of claim 23 in which the narrower included wavelength range is less than about 3 nanometers and changes the total emissions by approximately 1% as measured from the total fluorescent emissions at a wavelength just below the narrower included wavelength range.

27. The apparatus of claim 23 in which the narrower included wavelength range is less than about 15 nanometers and changes the total emissions by approximately 5% as measured from the total fluorescent emissions at a wavelength just below the narrower included wavelength range.

28. The apparatus of claim 23 in which the analysis means includes means for taking a second derivative of the fluorescent emissions of the narrower included fluorescent emissions wavelength range.

29. The apparatus of claim 23 further comprising means for sampling at two discrete wavelengths within the narrower included fluorescent emission wavelength range to represent a minimum and a maximum level of emission which results in a two point linear approximation.

30. The apparatus of claim 23 in which the adjustable detection means comprises a narrow port chopper.

31. The apparatus of claim 23 in which the adjustable detection means comprises a wide port chopper.

32. The apparatus of claim 23 in which the adjustable detection means comprises a photo-sensitive linear array.

33. The apparatus of claim 23 in which the physical characteristic of the functional coating is selected from a list of characteristics including thickness, weight, uniformity, defects, and markings.

\* \* \* \* \*